(12) United States Patent
Dal Farra et al.

(10) Patent No.: US 8,541,374 B2
(45) Date of Patent: Sep. 24, 2013

(54) USE OF A COMPOSITION COMPRISING A NON-FERMENTED RICE PEPTIDIC HYDROLYZATE FOR STIMULATING HAIR GROWTH

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/505,488

(22) PCT Filed: Nov. 2, 2010

(86) PCT No.: PCT/FR2010/000722
§ 371 (c)(1),
(2), (4) Date: May 2, 2012

(87) PCT Pub. No.: WO2011/055032
PCT Pub. Date: May 12, 2011

(65) Prior Publication Data
US 2012/0214746 A1   Aug. 23, 2012

(30) Foreign Application Priority Data
Nov. 3, 2009   (FR) ...................................... 09 05256

(51) Int. Cl.
*A61K 38/00* (2006.01)
*A61P 17/14* (2006.01)

(52) U.S. Cl.
USPC ...................................................... 514/20.7

(58) Field of Classification Search
None
See application file for complete search history.

(56) References Cited

U.S. PATENT DOCUMENTS

| | | | | |
|---|---|---|---|---|
| 8,231,916 | B2 * | 7/2012 | Msika et al. | 424/750 |
| 2006/0141078 | A1 * | 6/2006 | Guillou et al. | 424/750 |
| 2009/0215685 | A1 * | 8/2009 | Nishimura et al. | 514/12 |

FOREIGN PATENT DOCUMENTS

| | | |
|---|---|---|
| AU | 663301 | 10/1995 |
| DE | 10 2004 001267 | 8/2005 |
| EP | 0728462 A2 * | 8/1996 |
| EP | 1656970 | 5/2006 |
| FR | 2684295 | 6/1993 |
| FR | 2704751 A1 * | 11/1994 |
| FR | 2888725 | 1/2007 |
| FR | 2895261 | 6/2007 |
| FR | 2915379 A1 * | 10/2008 |
| FR | 2915380 | 10/2008 |
| FR | 2915381 | 10/2008 |
| FR | 2915383 | 10/2008 |
| FR | 2915384 | 10/2008 |
| FR | 2944796 | 10/2010 |
| JP | 05-306211 | 11/1993 |
| JP | 2004-099503 | 4/2004 |
| WO | WO 2004112732 A2 * | 12/2004 |
| WO | 2010/055833 | 5/2010 |
| WO | 2011/015796 | 2/2011 |

OTHER PUBLICATIONS

PCT, International Search Report, International Application No. PCT/FR2010/000722 (mailed May 11, 2011; published Jun. 30, 2011).
"Kelisema S.r.l.—Active Ingredients for the Cosmetic Industry," XP002581578, www.prochem.ch/html/Kelisema.ppt (49 pages) (retrieved from the internet on May 7, 2010).
Bernard, B.A., "La vie révélée du follicule de cheveu humain," Medecine/Sciences, No. 2, vol. 22, pp. 138-143 (Feb. 2006).
Birch, M.P. et al., "Hair density, hair diameter and the prevalence of female pattern hair loss," British Journal of Dermatology, vol. 144, pp. 297-304 (2001).
Chikh, A. et al., "Expression of GATA-3 in epidermis and hair follicle: Relationship to p63," Biochemical and Biophysical Research Communications, 361, pp. 1-6 (2007).
Das Gupta, R. et al., "Multiple roles for activated LEF/TCF transcription complexes during hair follicle development and differentiation," Development, 126, pp. 4557-4568 (1999).
Osborne, The Vegetable Proteins, pp. 68-154 (1924).
Tsuruki, T. et al., "Anti-alopecia mechanisms of soymetide-4, an immunostimulating peptide derived from soy β-conglycinin," PEPTIDES, Elsevier, Amsterdam, vol. 26, No. 5, pp. 707-711 (May 1, 2005).
Van Mater, D. et al., "Transient activation of β-catenin signaling in cutaneous keratinocytes is sufficient to trigger the active growth phase of the hair cycle in mice," Genes & Development, 17, pp. 1219-1224 (2003).
Excerpt from Principles of Polymer Science and Technology in Cosmetics and Personal Care, E. Desmond Goddard and James V. Gruber, 1999, Marcel Dekker Inc., pp. 410-411 (available at http://books.google.com/books?id=56R-6Wyyo6IC&pg=PA410&dq=hydrolysates+of+a+globular+protein+are+peptides&hl=en&sa=X&ei=rAqAUeKCLrbj4AO4-IHIDQ&ved=0CDsQ6AEwAO#v=onepage&Q&f=false).

* cited by examiner

*Primary Examiner* — Cecilia J Tsang
*Assistant Examiner* — Zachary J Miknis
(74) *Attorney, Agent, or Firm* — Thompson Hine L.L.P.

(57) ABSTRACT

The present invention relates to the use of a composition comprising at least one non-fermented rice peptidic hydrolyzate as an active agent for slowing down and limiting hair loss and/or stimulating hair growth. Said composition is also intended to protect the follicular adult stem cells as well as their specific microenvironment. In addition, the composition according to the invention combats the aging and particularly the photoaging of hair. Lastly, the present invention relates to several non-therapeutic treatment methods utilizing said composition.

13 Claims, 1 Drawing Sheet

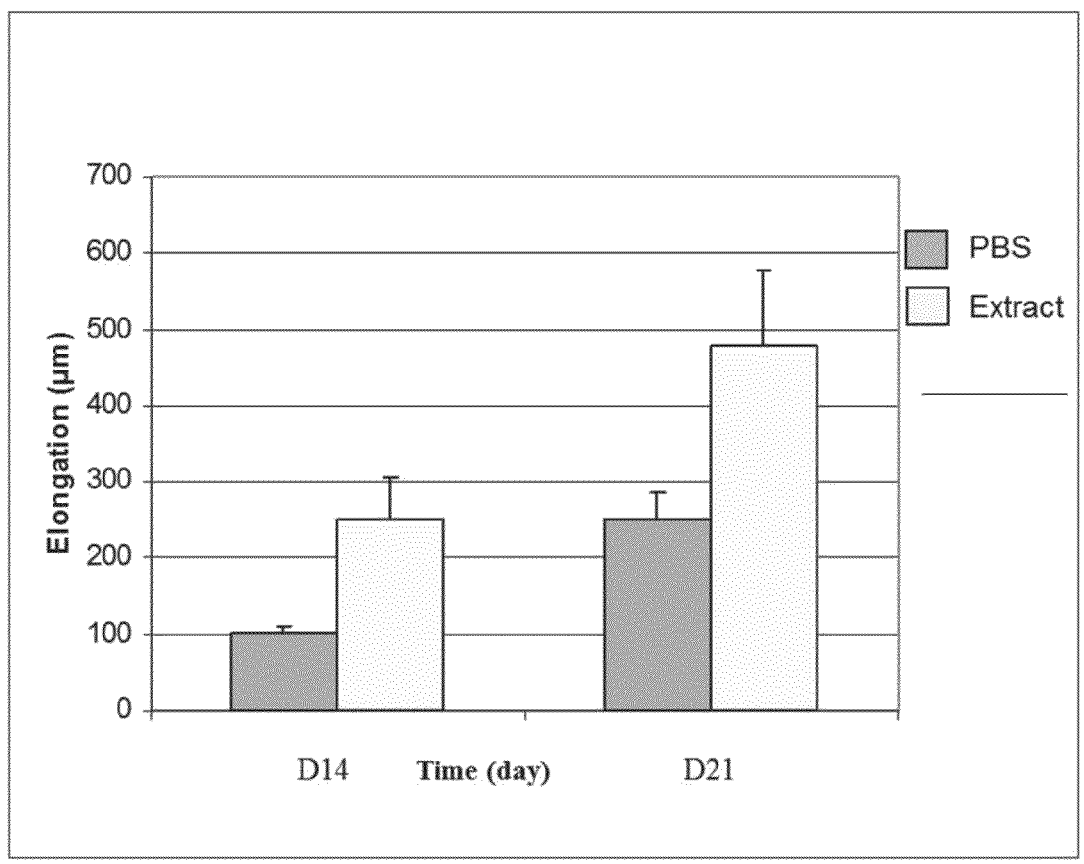
Hair elongation measurement after treatment with the non-fermented rice peptide extract

USE OF A COMPOSITION COMPRISING A NON-FERMENTED RICE PEPTIDIC HYDROLYZATE FOR STIMULATING HAIR GROWTH

The present invention is situated in the field of cosmetic and pharmaceutical compositions applied to the hair. The present invention relates to the use of a composition comprising at least one non-fermented rice peptidic hydrolyzate to slow down and limit hair loss and/or stimulate hair growth, as well as several non-therapeutic treatment methods using said composition.

Hair is a keratin annex, in the same capacity as eyelashes, eyebrows or else nails. Hair plays a physiological role in protecting the scalp, but above all has played a social role for a long time in the history of man. There are different types of hair, long, short, straight, curly . . . but all hair obeys the law of the cycle. In fact, the 100,000 to 150,000 hair follicles that form "normal" hair all renew cyclically, asynchronously and stochastically from a reservoir of follicular adult stem cells.

The hair follicle is an autonomous cutaneous annex with its own hormonal control, its own cycle and a complex and stable structure (Bernard B. A.; *Médecine/Sciences* 2006; 22: 138-43). The hair cycle is broken down into 3 phases: The anagen, catagen and telogen phases. The anagen, or hair growth phase, lasts between 3 and 7 years (variable depending on the age, sex and area of the scalp). This phase is followed by a phase of rest called the catagen phase that lasts approximately 3 weeks. While the apoptosis process takes place during this catagen phase, therefore leading to hair loss, the next phase, called the telogen phase, will enable a new bulb to be formed from a hair germ that will initiate the following cycle (Arouete J., J. *Med. Esth. Et Chir. Derm.,* September 2005, 119, 165-167). This telogen phase will last approximately 3 months. Therefore, in "normal" hair, approximately 85% of follicles are in the growth phase, 2% are in the rest phase and a little over 10% are in the loss phase.

For both men and women, it is normal to lose 100 to 150 hairs per day. The hairs fall and renew themselves. But when the loss easily exceeds 150 hairs, or when renewal by another follicle is faulty (very fine or thin hair), it is then called hair loss, also called alopecia. Alopecia refers to the complete or partial loss of hair, definitive or transient, due in particular to age, genetic factors or based on a local or general condition. Different types of alopecia may be distinguished depending on the origin of the problem:

androgenetic alopecia (often hereditary) is the most frequent: it is manifested by a reduction in hair volume, or even baldness, and affects 70% of men (but it also affects women);

acute alopecia: this may be connected to chemotherapy treatment, stress, significant food deficiencies, iron deficiency, hormonal problems or acute radiation;

localized alopecia: this may be caused by skin problems (tumors, burns, alopecia areata), radiotherapy or parasites (ringworm, lichen);

congenital alopecia;

alopecia areata, which appears to be of auto-immune origin (cellular mediation mechanism) that is characterized by a more or less large "patch" in one or more locations. This form of alopecia areata may reach the entire head, this is called alopecia totalis, and sometimes the entire body, this is called alopecia universalis (in this case, there is no longer any hair on the entire body).

Various cosmetic and/or drug treatments have been developed over these last few years to best treat the different types of alopecia. Most treatments exist for androgenetic alopecia, since this type of alopecia affects the most people. The origin of this type of alopecia is due to a very high sensitivity to the masculine or androgen hormones, itself due to heredity. Under the influence of an enzyme, 5-alpha-reductase, testosterone is transformed into dihydrotestosterone or DHT that will stimulate the sebaceous glands. Therefore permanent seborrhea is created, that will lead to the progressive obstruction of the hair follicle and asphyxia of the bulb, with the sudden suspension of the anagen phase as the consequence.

Among the treatments proposed for treating this type of alopecia, Minoxidil, or else Propecia® may be cited. The first enables the end of the growth cycles to be delayed and indirectly acts on the hair loss. However, it has many disadvantages, such as the fact that it must be administered very early during the onset of alopecia, or else that, the hair loss starts again once the treatment has been stopped. Propecia®, or finasteride, is an agent blocking the enzyme responsible for the conversion of testosterone into dihydrotestosterone at the hair follicles. It enables the hair loss to be reduced and activates hair regrowth. But one of the major disadvantages of this compound resides in its risk of causing an increase in the incidence of prostate cancer. In addition, its contraindication for treating alopecia in females limits its field of application.

Cosmetic oriented compositions have been proposed to mitigate the lack of medical treatments for androgenetic alopecia. Certain compositions are more or less intended to increase the apparent volume or density of hair. Other compositions are intended to more or less stimulate the growth and health of hair by increasing the synthesis of key proteins in hair formation. However, a high demand for compositions that limit hair loss and/or stimulate hair growth currently exists.

Thus, the applicant has demonstrated the properties as an anti-hair loss agent of a particular rice extract, particular in that the extract is a peptidic hydrolyzate coming from the hydrolysis of rice grain proteins, said rice being non-fermented.

For a long time, rice has been known to be an agent stimulating the growth of hair with more or less effectiveness. For example, a composition, comprising a rice extract as a promoter of HGF growth factor production, was described as a hair growth activator (JP patent 2004099503A). A Japanese patent filed by SO-KEN KK (JP5306211A) describes a tonic composition having anti-hair loss properties, said composition comprising an aqueous or organic extract of rice obtained by amylase decomposition. Other patent publications and/or applications describe rice extracts stimulating hair growth, such as the application of FR patent 2684295. In this application, the rice extract is obtained from its grain of rice and is followed by a fermentation step. However, none of these extracts is a peptide extract issued from the hydrolysis of non-fermented rice grain proteins to combat hair loss and preserve hair health. The closest prior art to the invention consists of a rice peptide extract, intended for the treatment and prevention of skin aging (patent applications FR 2915379, FR 2915380, FR 2915383). The rice peptide extracts described in these patent applications are not expressly non-fermented. In addition, it is never described or suggested that the compositions disclosed are intended for the treatment of hair loss.

Therefore, the first object of the present invention refers to the cosmetic use of a composition comprising at least one non-fermented rice peptidic hydrolyzate coming from the hydrolysis of rice grain proteins, as an active agent for slowing down and limiting hair loss and/or stimulating hair growth.

The second object of the present invention refers to the use of a composition comprising at least said hydrolyzate as an active agent to protect follicular adult stem cells as well as their specific micro-environment.

A third object of the present invention is the use of a composition comprising at least said hydrolyzate as an active agent to combat aging, in particular photo-aging, of hair.

Other objects of the present invention refer to non-therapeutic treatment methods intended to slow down or limit hair loss and/or stimulate hair growth, protect the follicular adult stem cells as well as their specific micro-environment, prevent aging, in particular photo-aging of hair, and lastly protect the hair and the hair shaft from external stresses.

FIG. 1 represents a histogram compiling and comparing the results of an elongation study of hair follicles in the presence or not of the non-fermented rice peptidic hydrolyzate according to the invention.

Therefore, the present invention refers to the use of a composition comprising at least one non-fermented rice peptidic hydrolyzate coming from the hydrolysis of rice grain proteins, as an active agent for slowing down and limiting hair loss and/or stimulating hair growth.

According to the invention, the terms "peptidic hydrolyzate," "extract," "peptidic extract," "solubilized extract" or "active agent" will be used equally.

"Peptidic hydrolyzate" is understood to refer to an extract obtained by the hydrolysis of rice grains, comprising a mixture of compounds predominantly represented by peptides or oligopeptides. "Non-fermented rice peptidic hydrolyzate" is understood to refer to a hydrolyzate obtained from rice grain proteins not having undergone a fermentation step, either before the hydrolyses or after obtaining the hydrolyzate.

The applicant discovered that a peptidic extract of non-fermented rice presents a certain activity on hair follicles and, in particular, had an action as an anti-hair loss agent. Many rice extracts exist in this indication but these extracts are most of the time glucosidic extracts, the proteins and peptides present being deliberately destroyed when the extract is obtained. The use of a non-fermented extract enabled the applicant to optimize its biological performance, in quantitative and qualitative terms, with relation to existing rice extracts. Thanks to the non-fermentation of rice grains, the proteins composing them are not degraded by the proteases of fermentation yeast. Therefore, a maximum of native proteins is retained and it will be easy to selectively and specifically hydrolyze them in order to obtain a large number of bioactive peptides.

"Active agent to slow down and limit hair loss and/or stimulate hair growth," is understood to refer to any non-fermented rice peptidic hydrolyzate that may stimulate the hair follicle, α6-integrin expression, keratinocyte differentiation markers such as keratin K15, or else β-catenin, or else proliferation markers such as p63.

The human keratin fibers to which the invention applies are, in particular, hair, eyebrows, eyelashes, beard, mustache and pubic hair and nails. According to a particular embodiment, the composition is intended to be used to activate eyelash growth.

A second object of the invention refers to the use of at least one rice peptidic hydrolyzate according to the invention as an active agent to protect follicular adult stem cells as well as their specific micro-environment. The hydrolyzate according to the invention was tested by the applicant, and the applicant could demonstrate its biological action on the cells forming the hair follicle, particularly the follicular adult stem cells. It was demonstrated that the extract had, more specifically, an action on the specific microenvironment constituting the "niche" that protects said stem cells. Lastly, an action of protecting these same cells by said extract was demonstrated.

It is known that adult stem cells, particularly follicular adult stem cells, are difficult to identify. However, they are nevertheless distinguishable since they express a set of markers that enable a specific expression profile for this cell type to be obtained. From these markers, the following are found, among others:

keratin K15 that is a marker of stem cells in the most differentiated stage in the follicular compartment called the bulge (Bernard B. A.; *Médecine/Sciences* 2006; 22: 138-43);

α6 integrin (that colocalizes with Laminine-5) that is described as being a potential marker of follicular stem cells (Bernard B. A.; *Médecine/Sciences* 2006; 22: 138-43);

β-catenin that plays a key role in the differentiation and growth of the hair follicle (DasGupta and Fuchs, 1999, *Development* 126:4557-68; Van Mater et al., 2003, *Gene dev.* 17:1219-24);

p63 that is a marker connected to the proliferative ability of stem cells to generate a follicle, a sebaceous gland and an epidermis (Chikh et al., 2007, *Biochem Biophys Res Commun.*, 14; 361(1):1-6.

The hydrolyzate according to the invention demonstrated its action on the different markers cited above. In fact, an increase in the expression of these markers is assisted when a composition comprising at least said hydrolyzate is applied to the follicles in culture. The consequence of these overexpressions results in a limitation in hair loss, and subsequently, a stimulation in hair growth.

A third object of the present invention relates to the use of at least one hydrolyzate according to the invention as an active agent to combat aging, in particular photo-aging, of hair. It is known that the aging of hair is essentially manifested (besides its graying) by a lowering in capillary density and by the progressive reduction in follicle diameter, giving the hair a poorer, more sparse appearance (Pelfini, C. et al., J. *Méd. Esth. Et Chir. Derm* 1987; Birch MP et al. Br. J. *Dermatol* 2001; 144:297-304). Moreover, besides the conventional genetically programmed aging, there is photoaging, that itself is caused by the accumulation of stresses due to UV radiation and that results in a premature deterioration of the hair structure and in follicle depletion. Consequently, the use of an extract that protects the follicular adult stem cells will have the effect of preventing aging, particularly premature aging, and notably photoaging.

According to an advantageous mode of embodiment of the invention, the hydrolyzate comes from the hydrolysis of grain proteins from *Oryza Sativa L*. rice. The peptidic hydrolyzate is constituted of a mixture of compounds predominantly represented by peptides. The term "peptide" designates a chain of two or more amino acids interlinked by peptide linkages or by modified peptide linkages. The term "polypeptide" designates a peptide with a larger size. The utilization of peptidic hydrolyzates, particularly low molecular weight peptidic hydrolyzates, presents many advantages in cosmetics. In addition to generating peptidic nature compounds that did not preexist in the starting protein mixture, hydrolysis and purification enable more stable mixtures to be obtained, that are easy to standardize and that do not cause dermatological and cosmetic allergic reactions.

The hydrolyzate according to the invention is obtained by extraction of non-fermented rice proteins, the extraction followed by a controlled hydrolysis that releases bioactive peptide fragments. Very many proteins found in plants are likely to contain bioactive peptide fragments within their structure. Controlled hydrolysis enables these peptide fragments to be released. It is possible, but not necessary to carry out the invention, to extract either the relevant proteins first and then hydrolyze them, or perform hydrolysis first on a crude extract and then purify the peptide fragments. It is also possible to use certain hydrolyzed extracts without purifying the peptide fragments corresponding to the bioactive peptides according to the invention, but by ensuring the presence of said peptides by suitable analytical means.

Extraction Protocol

To carry out the extraction, the whole plant or a specific part of the plant (leaf, seed, etc.) may be used.

More specifically according to the invention, one of the many plants from the Poaceae family of the genus *Oryza* (rice), and preferentially the species *Oryza sativa* L. is used. According to the invention, the plant material utilized will be the seed and the hull of the seed was removed by a hulling step.

In a first step, the plant is ground by using a plant grinding mill. The powder thus obtained may subsequently be defatted by using a conventional organic solvent (such as for example an alcohol, hexane or acetone). As mentioned previously, the grains do not undergo any fermentation step, therefore the extract remains concentrated in native proteins.

Then proteins are then extracted according to a modified conventional method (Osborne, 1924); the plant ground material is suspended in an alkaline solution containing an adsorbent product of the insoluble polyvinylpolypyrrolidone (PVPP) type (0.01-20%); In fact, it was observed that subsequent hydrolysis and purification operations were facilitated by this means. In particular, the concentration of phenolic type substances, interacting with proteins, is markedly reduced.

The soluble fraction, containing proteins, carbohydrates and possibly lipids, is collected after the centrifugation and filtration steps. This crude solution is then hydrolyzed under controlled conditions to generate peptides. Hydrolysis is defined as being a chemical reaction involving cleavage of a molecule by water, this reaction may be done in neutral, acidic or basic medium. According to the invention, hydrolysis is carried out chemically and/or advantageously by proteolytic enzymes. The utilization of plant origin endoproteases (papain, bromelin, ficin) and microorganisms (*Aspergillus, Rhizopus, Bacillus*, Novozyme Alcalase®, etc.) may then be cited.

For the same reasons as above, i.e., the elimination of polyphenolic substances, a quantity of polyvinylpolypyrrolidone is added to the reaction medium during this controlled hydrolysis step. After the filtration step, enabling the enzymes and polymers to be eliminated, the filtrate (solution) obtained constitutes a first form of the active agent according to the invention.

We then proceed to a dilution phase. Therefore, the extract is solubilized in one or more physiologically suitable solvents, such as water, glycerol, ethanol, propylene glycol, butylene glycol, dipropylene glycol, ethoxylated diethylene glycol or propoxylated diethylene glycol, cyclic polyols or any mixture of these solvents. This dilution step is followed by sterilization by ultrafiltration to obtain a peptide extract characterized by a peptidic nature compound content of 1.5 to 4 g/l. Preferentially, the extract obtained comprises a content in these same compounds of between 2 and 3 g/l.

The hydrolyzate obtained at this stage may be purified again in order to select the low molecular weight fractions, preferentially lower than 6 kDa. Therefore, at least 70% of peptidic nature compounds present in the extract are peptides with a size of less than 6 kDa, and preferentially at least 85%. Purification is advantageously carried out by successive ultrafiltration steps through filters of decreasing porosity, by conserving the filtrates at each step and/or by a chromatographic type method.

Therefore, according to an advantageous mode of embodiment of the invention, the peptide extract has a pH of between 4 and 7, and preferentially between 5 and 6, the dry extract titers from 2 to 5 g/l and preferably between 3 to 4 g/l, its peptidic nature compound content is between 1.5 and 4 g/l, and preferentially between 2 and 3 g/l and its sugar content is between 0.5 to 1 g/l.

According to a second mode of embodiment of the invention, the solubilized extract may be encapsulated or put in a cosmetic or pharmaceutical carrier such as liposomes, or any other microcapsule used in the cosmetic field, or adsorbed on powdery organic polymers, mineral supports such as talcs and bentonites, and more generally solubilized in, or fixed on, any physiologically acceptable carrier.

Therefore, the solubilized extract is used in compositions according to the invention at a concentration of between approximately 0.001% to 5%, and preferentially at a concentration of between approximately 0.01% and 1% with relation to the total weight of the final composition.

Preferentially, the composition according to the invention is present in a form that is suitable for topical application.

The usable composition according to the invention may in particular consist of a composition for hair care, particularly a shampoo, conditioner, setting lotion, pre- or post-aggressive hair treatment treating lotion, styling cream or gel, hair restructuring lotion, mask, treating foam, etc.

The composition may in particular be in cream, oil-in-water emulsion, water-in-oil emulsion form or multiple emulsions of the oil-in-water-in-oil or water-in-oil-in-water type, suspension, aqueous gel, hydroalcoholic or oily aqueous solutions. The composition may be more or less fluid and present in the form of a white or colored cream, pomade, milk, lotion, serum, foam, biphase, or else in aerosol form.

Lastly, the composition may comprise any additive commonly utilized in the contemplated field of application as well as the adjuvants necessary for their formulation, such as co-solvents (ethanol, glycerol, benzyl alcohol, humectants, etc.), thickeners, diluents, emulsifiers, antioxidants, colorants, sunscreens, pigments, fillers, preservatives, fragrances, odor absorbers, essential oils, trace elements, essential fatty acids, surface active agents, film-forming polymers, chemical or mineral filters, moisturizing agents or thermal waters, etc. For example, one may cite hydrosoluble polymers of the natural polymer type, such as polysaccharides or polypeptides, cellulosic derivatives of the methylcellulose type or hydroxypropylcellulose type, or else synthetic polymers, poloxamers, carbomers, PVA or PVP and particularly the polymers sold by the ISP company.

In all cases, the person skilled in the art will make sure that these adjuvants as well as their proportions are chosen so as to not harm the desired advantageous properties of the composition according to the invention. These adjuvants may, for example, correspond to 0.01 to 20% of the total weight of the composition. When the composition according to the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

In addition, the composition according to the invention may also comprise at least one compound improving hair growth and/or health.

In particular, vitamins, other plant peptidic hydrolyzates, minoxidil, nicotinic acid esters, trace elements, anti-inflammatory agents, retinoic acid or its derivatives, retinol, 5α-reductase inhibitors or peptide compounds from chemical synthesis may be cited. As samples of vitamins, vitamins A, E, B5, B6, C, H, or PP may be cited; As examples of trace elements, zinc, copper, magnesium or else silicon may be cited.

One particular mode of embodiment of the invention refers to the use of a composition comprising, in addition to the non-fermented rice peptidic hydrolyzate, a soy peptidic hydrolyzate. Tests carried out on skin biopsies have demonstrated the protective effect of this combination of extracts with regard to UV radiation, and these results may be extrapolated and applied to the cells from the outer root sheet or ORS.

In final, the composition according to the invention is composed of between 10 and 90% of a non-fermented rice hydrolyzate, and between 10 and 90% of a soy hydrolyzate. Preferentially, the composition respectively comprises 90% non-fermented rice hydrolyzate and 10% soy hydrolyzate. The rice and soy hydrolyzates may be obtained separately and then incorporated into the composition, or else be produced at the same time in one and the same hydrolyzate, this single hydrolyzate being subsequently incorporated into the composition.

Through its particular activities, the extract according to the invention may be used as a medication. Therefore, the extract may be used to produce a pharmaceutical composition intended to slow down and limit hair loss and/or stimulate hair growth in the case of hair loss resulting from a pathological condition. In fact, the extract may be incorporated in a pharmaceutical composition to slow down hair loss or stimulate hair growth in the case of alopecia areata, or else alopecia caused by skin conditions such as burns or else parasites.

A fourth object of the present invention refers to a non-therapeutic treatment method intended to slow down and limit hair loss and/or stimulate hair growth, characterized in that a composition according to the invention is applied daily to the scalp area to be treated.

Another object of the present invention relates to a non-therapeutic treatment method intended to protect follicular adult stem cells, as well as their specific microenvironment, by applying a composition such as described previously daily to the scalp area to be treated.

Another object of the present invention relates to a non-therapeutic treatment method intended to prevent aging of the hair, in particular photoaging, by applying the composition according to the invention daily to the scalp area to be treated. As mentioned previously, before the hair completely disappears, aging of the hair is manifested by a reduction in capillary density, miniaturization of hair follicles, depletion and thinning of hair and, finally, graying that leads to canities. Such being the case, the composition comprising the hydrolyzate according to the invention demonstrated that it may limit the natural aging phenomenon of hair thanks to the preservation of stem cells in particular, and of their specific microenvironment. In addition, the use of the composition to prevent damage caused by UV radiation has proved its interest in preventing photo-aging. This is why, for example, the hydrolyzate may be advantageously used in a composition as a photoprotective agent and, more particularly, as a photoprotective agent called a "secondary" agent. In fact, primary photoprotective agents can be distinguished from secondary photoprotective agents. Primary photoprotective agents are substances that exert a physical power: They are capable of absorbing UV radiation and release it in the form of heat in order to protect the skin and epithelial appendages. Secondary photoprotective agents are substances that generally have a biological effect; They are, for example, agents capable of limiting damage caused to the DNA and to the cell membranes by UV radiation penetration.

Lastly, a last object of the present invention refers to a non-therapeutic treatment method intended to prevent damage to and to protect the hair and hair shaft from external stresses, thanks to the application of a composition according to the invention, before exposure to the sun, to chemical products or heat sources, such as colorings, hair straightening, permanents or else blow-dryings. "External stresses" is understood to refer to stresses that the environment may produce. By way of example one may cite stresses such as pollution, UV radiation or else irritating products such as coloring, bleaching and hair straightening products, surface active agents, preservatives or fragrances. Pollution is understood to refer to both "external" pollution, due for example to diesel particles, ozone or heavy metals and to "internal" pollution, that may be particularly due to the emissions from paint, adhesive or wallpaper solvents (such as toluene, styrene, xylene or benzaldehyde), or else to cigarette smoke. It is known, particularly by hair styling professionals that, for example, chemical treatments attack the hair shaft and that, consequently, the use of hair care in pre-treatment enables the hair and scalp to be protected. For this purpose, the use of a composition comprising a non-fermented rice peptide extract therefore has a preventive and protective action.

Other advantages and characteristics of the invention will more clearly appear upon reading the examples given for illustrative and non-limiting purposes.

EXAMPLE 1

Method of Preparing a Non-Fermented Rice Peptide Extract

The extract according to the invention is obtained from plants of the species *Oryza sativa* L. Of course, the extract may be prepared from plants of at least any one of the many varieties and species belonging to the *Oryza* genus.

In a first step, 1 kg of hulled rice grains are ground in a cereal grinding mill. The flour obtained is de-fatted by the action of an organic solvent, hexane. After filtration and vacuum drying, the powder obtained is suspended in an alkaline aqueous solution (1:10 dilution) pH 10, containing 1% polyvinylpolypyrrolidone (Polyclar V ISP). This mixture is maintained under agitation for a sufficiently long time to enable solubilization of the soluble fractions. The extraction temperature is variable (between 4 and 80° C.); But preferentially, the operation will be carried out cold. After this extraction phase, the medium is clarified by centrifugation and then filtered on a plate filter. This filtrate that contains soluble rice fractions is then subjected to protein precipitation by varying the ionic strength in neutral or acidic medium, which enables soluble glucidic components, lipids and nucleic acids to be eliminated. The medium is brought to pH 3.5. The supernatant is eliminated and the precipitate is then washed by using a solvent such as, for example, ethanol or methanol. Lastly, the solvent is evaporated by vacuum drying.

At this stage, approximately 50 grams of pale yellow crude protein extract powder are obtained containing:
Proteins: 75%
Carbohydrates: 20%
Lipids: 5%

The protein-rich precipitate is put back in solution in water or another solvent.

The crude protein extract is then subjected to a series of controlled and selective hydrolyses consisting of chemical and enzymatic hydrolyses in the presence of 0.5% PVPP (Polyclar V) and cysteine endopeptidases (papain, ficin). After reaction, the hydrolyzate is filtered on a plate and then on sterilizing cartridge (0.2 µm).

A pale hydrolyzate is then obtained, titrating from 15 to 30 g/l of dry extract, that is then diluted such that the concentration of peptidic nature compounds determined by the Lowry method is between 0.1 and 5 g/l and preferentially between 0.5 and 2 g/l.

The solution is then ultrafiltrated on a Millipore Helicon filtration cartridge (cutoff; 6 kDa). The high molecular weights contained in the retentate are separated, the filtrate is retained. After analysis, particularly by HPLC, it is observed that the extract contains approximately 80% peptidic compounds with a size of less than 6 kDa.

Another variation of the method for obtaining the extract consists of purifying the extract previously obtained by ion exchange chromatography on a TSK gel column (TosoHaas) with a phosphate buffer pH 7.

The extract obtained according to the method described in example 1 is then solubilized in glycerol.

EXAMPLE 2

Method of Preparing a Mixture of a Non-Fermented Rice Peptide Extract and a Soy Peptide Extract The rice and soybean cake flour is previously put in solution, respective proportions of 90:10, in 20 volumes of water adjusted to a pH of between 8.0 and 8.5. After adjusting the pH, 2% bromelin, 2% Alcalase® and 2% POLYCLAR® 10 (polyvinylpyrrolidone-PVPP-insoluble) are added to the reaction medium. The reaction medium is then heated two hours at 50° C. and then deactivated two hours at 80° C. A filtration step recovers the filtrate composed of 20 to 25 g/L of dry matter, 18 to 22 g/L of proteins and 2 to 3 g/L of sugars.

The protein nature of this filtrate is demonstrated by electrophoresis on polyacrylamide gel. For this analysis, NuPAGE® Bis-Tris Pre-cast (Invitrogen) gels are utilized. The rice-soy intermediate protein extract is heated to 70° C. for 10 minutes under reducing denaturing conditions in a NuPAGE® LDS sample preparation buffer. A NuPAGE® Antioxidant solution is added into the inner tank (cathode) to prevent the reduced proteins from reoxidizing during electrophoresis. Protein migration is carried out by using the NuPAGE® MES migration buffer with the standard SeeBlue Plus2 as a molecular weight marker. Protein staining is carried out by using Coomassie Blue® R-250. The protein profile thus obtained demonstrates a distribution of molecular weight of between 15 and 3 kDa.

The intermediate rice-soy protein extract previously obtained is then purified by successive filtrations by using Seitz-Orion filter plates of decreasing porosity (up to 0.2 µm) in order to obtain a bright and clear pale yellow solution. In this step, the rice-soy extract is characterized by a dry extract of 20-24 g/kg, a protein level of 18-21 g/L and a sugar level of 1-3 g/L.

This solution is then purified by eliminating proteins of molecular weight greater than 5 kDa by using tangential flow filtration.

To do this, the rice-soy solution is pumped under pressure through a Pellicon® support equipped with a Pellicon® 2 Biomax cassette 10 kDa. This 1st filtrate is recovered to then be filtered through another Pellicon® 2 Biomax cassette 3 kDa. At the end of purification, a bright and clear pale yellow rice-soy plant extract is obtained. It is characterized by a dry extract of 17-20 g/kg, a protein content of 15-18 g/L and a sugar level of between 1 and 2 g/L.

This solution is then analyzed by high pressure liquid chromatography (HPLC) by using an HP1100 apparatus run by the ChemStation software. The column utilized during elution of the rice-soy extract is a Nucleosil® 300-5 C4 MPN (125×4 mn) column. This column enables proteins having molecular weights of 0.2 to 25 kDa to be chromatographed (according to a suitable solvent gradient). Under these chromatographic conditions, several peptidic fractions were isolated. These various fractions were analyzed by mass spectrometry to identify their molecular peaks. The amino acid content of the composition was also determined. This is obtained after acid hydrolysis and identification by high pressure liquid chromatography by using pre-derivation with PICT (phenylisothiocyanate).

EXAMPLE 3

Action of the Non-Fermented Rice Peptide Extract on Follicles Maintained in In Vitro Culture 3.1 Keratin K15 Labelling Hair Follicle Cultures and Inclusion of Sections Skin biopsies (from facelifts) presenting hair are cultivated in the same way as the skin explants. 6-mm biopsies are made by means of a biopsy punch and are cultured on inserts in a William's E medium in the presence of antibiotics (Penicillin 100 UI/ml-10 µg, streptomycin, 10 µg/ml insulin 10 nG/ml, Hydrocortisone and 2 mmol/L de L-Glutamine).

The skin explants are deposited in 6-well plates and the follicles are treated or not treated by putting 20 µl of extract at 1% in contact on the biopsies, after 48 hours of culture. At the end of the experiment, the biopsies are placed on a cassette and immersed in a mixture of formol at 10% for 2 hours in an automated apparatus (VIP). The cell coating by using paraffin is prepared by a series of alcohol baths (at increasing concentration and time), followed by 2 xylene baths and lastly by a paraffin bath. The total duration of this series of operations is a dozen hours. The biopsies thus coated are then placed in the appropriate cassettes, oriented and put in a paraffin block to then be cut in 4 µm sections by a microtome.

The paraffin is then removed from the paraffined sections and the sections are rehydrated before the placement of antibodies. To do this, a series of xylene baths, followed by a series of alcohol baths (at increasing concentrations and times) and rinsing in water, and then in PBS are carried out for this purpose.

Keratin K15 Immunolabelling

The deparaffined sections are rinsed in PBS for 2 minutes, then surrounded and each section is incubated in 100 µl of BSA 5% for 30 minutes. Then, 100 µl of Cytokeratin K15 primary antibody (Abcam, Mouse monoclonal) is added and agitated for 60 minutes in a humidity chamber. After rinsing with PBS for 30 minutes, 100 µl of fluorescence-labelled secondary antibody is added and left for 1 hour in darkness under agitation in a humidity chamber. These labellings are carried out in parallel on the biopsies that are treated or not treated with the active peptide extract. The slides are then rinsed in PBS, mounted between slide and coverslip in Aquatex, and the observation is carried out by epifluorescence microscope.

Results

Thanks to fluorescence quantification software, an increase on the order of 95.3% of keratin K15 is observed in the hair follicles treated by using the active extract with relation to the untreated follicles. Such being the case, keratin K15 is implicated in the early keratinocyte differentiation stages in the hair follicles.

3.2 α6 Integrin Labelling

In order to carry out α6 integrin labelling in the hair follicles, facelift biopsies are carried out as described in example 3.1. The skin explants are deposited in 6-well plates and the follicles are treated or not treated by placing 20 µl of active extract in contact on the biopsies, after 48 hours of culture. Subsequently, in order to prepare the antibody labelling, the sections are not paraffinized but are placed in OCT (optimum cutting temperature) and cut in the cryostat (frozen section). Biopsies are then taken and included in the OCT that solidifies in cold (at −20° C.), and the blocks thus solidified are then cut by cryotome, where 6 µm-sections are made. The sections are collected on polylysinated observation slides. The sections with OCT are placed in ambient temperature before being used for immunolabelling.

α6 Integrin Immunolabelling

The slides mounted in OCT are dried in the chamber at 37° C. for 30 minutes, and then the sections are fixed in an acetone bath (previously maintained at −20° C.) for 10 minutes. The slides are rinsed in PBS for 5 minutes and then the sections are surrounded by the PAP pen. The sections are saturated by adding BSA at 5% for 30 minutes, and then the labelling with the primary antibody is carried out as described previously. Labelling is carried out thanks to an anti-α6 integrin antibody (Tebu Santa Cruz, mouse monoclonal). This first labelling is followed by a secondary labelling by a fluorescence-labelled antibody. Mounting the slide in a suitable medium and then reading it by an epifluorescence microscope enables the intensity of the labelling to be determined. This labelling is carried out in parallel on biopsies that are treated or not treated with the active extract to determine the effect of the latter on said biopsies.

Results

Treating follicles with the peptide extract from non-fermented rice strongly increases the quantity of α6 integrin. An increase of 108% of the quantity of α6 integrin with relation to untreated follicles is observed. Such being the case, it is known that α6 integrin is one of the potential markers for follicular stem cells.

3.3 β-Catenin Labelling

The same protocol (as that described in example 3.2) was used in order to carry out β-catenin labelling (Abcam anti-beta-catenin primary antibody followed by a fluorescence-labelled secondary antibody) and, here also, an increase in the β-catenin labelling in the follicles treated with the peptide extract with relation to untreated follicles is observed. Such being the case, it is known that β-catenin plays a key role in the differentiation and growth of hair follicles.

3.4 Protein p63 Labelling

The same protocol as that described in example 3.2 was used in order to carry out p63 protein labelling by using an anti-p63 primary antibody, mouse monoclonal TEBU Santa Cruz. This primary antibody labelling is followed by a secondary labelling by a fluorescence-labelled antibody. Mounting the slide in a suitable medium and then reading it by an epifluorescence microscope enables the intensity of the labelling to be determined. This labelling is carried out in parallel on biopsies that are treated or not treated with the active extract to determine the effect of the latter on said biopsies.

Results:

The follicles treated for 48 hours with the peptide extract present a much increased p63 protein labelling with relation to the untreated follicles. In fact, thanks to fluorescence quantification by suitable software, an increase of 13.6% of p63 labelling in treated follicles is observed. Such being the case, it is known that the p63 protein is a follicular stem cell marker connected to the capacity of these cells to generate a hair follicle.

3.5 Conclusions

The 4 labellings carried out on the hair biopsies demonstrated to us that the treatment of hair follicles by a non-fermented rice peptide extract would enable:

the quantity of proteins that are follicular stem cell markers to be increased;

consequently, the microenvironment of the stem cells and thus their protection to be encouraged;

and finally the differentiation and thus entrance of follicular stem cells into the anagen phase to be encouraged in order to best stimulate hair growth and/or slow down hair loss.

EXAMPLE 4

Action of the Peptide Extract on Follicles in the Presence of UV Radiation

Skin biopsies (from facelifts) presenting hair are cultivated in the same way as the skin explants. 6-mm biopsies are made by means of a biopsy punch and are cultured on inserts in a William's E medium in the presence of antibiotics (Penicillin 100 UI/ml-10 µg, streptomycin, 10 µg/ml insulin 10 nG/ml, Hydrocortisone and 2 mmol/L de L-Glutamine).

The skin explants are deposited in 6-well plates and the follicles are treated by putting 20 µl of extract at 1% in contact on the biopsies for 24 hours. The biopsies are then subjected to UVA radiation at 5 J/cm$^2$, followed by UVB radiation at 200 mj/cm$^2$, and lastly returned for 24 additional hours in the presence of the active extract. Control containers with explants untreated by the active peptide extract but irradiated are used as controls. An evaluation of the state of the cells after UV radiation is carried out by hematoxylin/eosin labelling.

Results

The general shape of the outer root sheet (ORS) is irregular in the follicles that were not pretreated and treated by the peptide extract, while the ORS is quite regular in the treated follicles. In addition, the untreated hair follicle cells present damage due to UVA and UVB radiation, damage such as the appearance of vacuoles, edema and apoptotic cells. All of these manifestations are not observed in the follicles pretreated and treated by the peptide extract. A protective role of this non-fermented rice peptide extract on hair follicles and, among others, on the stem cells of these follicles may thus be deduced.

EXAMPLE 5

Action of the Peptidic Hydrolyzate on Follicle Growth

Follicle Elongation Measurements

Skin biopsies from facelifts are shaved and then cultured in a suitable medium (William E. medium) In the presence or not of the active peptidic hydrolyzate at a concentration of 1%. In the absence of the active principle, the follicles are cultured in PBS. Photos are taken by using the Vivacam (small camera that equips the VIVASCOPE® confocal microscope for skin imaging) at time zero. The biopsies are recultured and hair follicle elongation measurements are taken on days 8, 14 and 21.

The photos at different times are then reprocessed by the "Image Pro Analyzer®" software that enables the size (in µm) of each follicle to be measured separately. The overall elongation of the treated and untreated follicles is measured and a statistical study is carried out and put together in the graph of FIG. 1.

Results:

At the end of this test, it is observed that the application of non-fermented rice peptidic hydrolyzate has an action on hair growth. In fact, it enabled more significant hair follicle growth with relation to the growth observed in untreated follicles.

EXAMPLE 6

Demonstration of the Protective Action of a Mixture of a Non-Fermented Rice Peptide Extract with a Soy Peptide Extract on Cells from Biopsies of Skin Subjected to UVB Radiation The goal of this experiment is to measure the capacities for restoration of a mixture comprising a non-fermented rice peptide extract in combination with a soy peptide extract (hereafter named rice/soy extract) after radiation by UVB radiation of human skin biopsies. It was demonstrated before that the results that will be obtained on the cells from skin biopsies correlate with those that would be obtained at the level of ORS cells. UV radiation, and particularly UVB radiation, leads to dimerization reactions that take place at the sites comprising two adjacent pyrimidines (thymidine, cytosine). Several types of photoproducts are then formed, including cylobutane-pyrimidine dimers or CPDs. Such being the case, it is known that when a cell is exposed to a genotoxic stress, its division cycle is temporarily suspended to enable the DNA to repair and to thus prevent the appearance of mutations in the following cell generations. The cellular proliferation only then restarts. If the frequency or quantity of damage is too high, or else the repair is ineffective, the cells launch a process of programmed death, apoptosis. This type of phenomenon is observed at the hair follicle cells and leads to death of the hair or to its loss of thickness. Consequently, by measuring by immunolabelling, by using anti-CPD antibodies, the quantity of photoproducts formed, it is possible to evaluate the effectiveness of a compound with a restorative action on the DNA of cells.

CPD Immunolabelling on Skin Biopsies Subjected to UVB Radiation Protocol

Human skin biopsies are cultured at the air/liquid interface and pretreated with the rice/soy extract at 1% for 24 hours, or with the placebo (PBS) for the control condition. These biopsies are subjected to UVB radiation at a rate of 200 mJ/cm². After radiation, the biopsies are recultured for 24 hours with only the application of PBS (i.e., without active agent). For labelling the cyclobutane-pyrimidine dimers, the skin biopsies are enclosed in paraffin and histological sections with a thickness of 3 µm are made. The paraffin is removed from the slides, the slides are hydrated and then subjected to immunolabelling directed against cyclobutane-pyrimidine dimers (MBL D194-1, mouse monoclonal) and then by a suitable secondary antibody (Invitrogen A21202) paired with a fluorescent marker. The skin sections are then examined by epifluorescence microscope (Nikon Eclipse E 80i microscope).

In the control condition, the fluorescence observed is more intense when the biopsies have been subjected to UVB radiation. In the tested condition with pretreatment by the rice/soy extract, a fluorescence that is much less intense than under the control condition with UVB is observed.

Conclusions:

This rice/soy extract enabled better protection of skin biopsies since less CPD type damage is observed in the biopsies pretreated by said extract. These results may thus be extrapolated and the conclusion may be made that the rice/soy extract according to the invention would have the same effects on ORS cells and would protect them from UV radiation.

EXAMPLE 7

Preparation of Compositions

1. Serum for Hair Growth

Disperse the NATROSOL® 250HHR hydroxyethylcellulose and the Disodium EDTA in water under agitation. Heat to 50-60° C., and agitate until a uniform appearance is obtained. Add the STYLEZE® CC-10 polymer and agitate until a uniform appearance is obtained. Allow to cool to ambient temperature and add the ingredients in the order listed by agitating until a uniform appearance between them is obtained.

| | | Formulations | | |
|---|---|---|---|---|
| INCI name | Trade name | No. 1 Weight percent | No. 2 Weight percent | Supplier |
| Water | | Qsp | qsp | |
| Hydroxyethyl-cellulose | NATROSOL ® 250HHR hydroxy-ethylcellulose | 0.35 | 0.50 | Hercules/Aqualon |
| Disodium EDTA | DISSOLVINE ® NA-2S sequestering agent | 0.05 | 0.05 | Akzo Nobel |
| VP/DMAPA Acrylates Copolymers | STYLEZE ® CC-10 polymer | 5.00 | 5.00 | ISP |
| Quaternium-26 | CERAPHYL ® 65 emollient | 1.00 | 1.00 | ISP |
| Panthenol | Ritapan DL | 0.15 | 0.15 | RITA |
| Propylene Glycol Diazolidinyl urea Iodopropynyl Butylcarbamate | LIQUID GERMALL ® Plus preservative | 0.50 | 0.50 | ISP |
| | Hydrolyzate according to example 2 | 1.00 | 1.00 | ISP |
| Total | | 100.00 | 100.00 | |

Apply the product to the damp scalp. Massage to distribute the product uniformly. The serum promotes hair growth and/or regrowth while making the hair more vigorous.

2. Anti-Hair Loss Treating Milk

Place water in a suitable container and start agitation. Add the GAFQUAT® 755N polyquaternium-11 and the LIQUID GERMALL® Plus preservative and agitate until a uniform appearance is obtained. Add the RAPITHIX™ A-60 rheology modifier and agitate until a uniform appearance is obtained (approximately 15 minutes). Add the hydrolyzate according to example 1 and agitate until a uniform appearance is obtained. Dispose the product in a non-aerosol vaporizer equipped with a Calmar Mark VI WL31 pump.

| INCI name | Trade name | Formulations | | Supplier |
|---|---|---|---|---|
| | | No. 1 Weight percent | No. 2 Weight percent | |
| Deionized water | — | qsp | qsp | |
| Polyquaternium-11 | GAFQUAT ® 755N polyquaternium LIQUID | 1.25 | 2.00 | ISP |
| Propylene Glycol Diazolidinyl urea Iodopropynyl Butylcarbamate | GERMALL ® Plus preservative | 0.50 | 0.50 | ISP |
| Sodium Polyacrylate Hydrogenated Polydecene Trideceth-6/ | RAPITHIX ™ A-60 rheology modifier | 0.50 | 0.50 | ISP |
| | Hydrolyzate according to example 1 | 0.1 | 0.5 | ISP |
| | Total | 100.00 | 100.00 | |

The product is designed to be vaporized onto the scalp and onto damp hair. Massage to distribute the product uniformly. The milk thus proposed combats hair loss while making the hair smooth and easy to style.

The invention claimed is:

1. A non-therapeutic method to slow down hair loss and stimulate hair growth, the method comprising:
    Providing a composition comprising at least one non-fermented rice peptidic hydrolyzate coming from the hydrolysis of rice grain proteins from the *Oryza sativa L* rice species, as an active agent, wherein at least 70% of the peptidic nature compounds present in the hydrolyzate are peptides with a size of less than 6 kDa; and
    applying the composition to a portion of the anatomy having hair follicles;
    where the non-fermented rice peptidic hydrolyzate results in an increase in β-cantenin labelling of the hair follicles thereby indicating an increase in the differentiation and growth of the hair follicles.

2. A non-therapeutic method to protect follicular adult stem cells as well as their specific microenvironment, the method comprising:
    providing a composition comprising at least one non-fermented rice peptidic hydrolyzate coming from the hydrolysis of rice grain proteins from the *Oryza Sativa L* rice species, as an active agent, wherein at least 70% of the peptidic nature compounds present in the hydrolyzate are peptides with a size of less than 6 kDa; and
    applying the composition to the scalp zone;
    wherein the composition protects follicular adult stem cells.

3. The method of claim 2, wherein the solubilized peptidic hydrolyzate comprises at least between 2 and 3 g/l of peptidic nature compounds.

4. The method of claim 2, wherein the solubilized hydrolyzate is used in a quantity representing from 0.01% to 1% of the total weight of the composition.

5. The method of claim 1, wherein the applying step is performed daily.

6. The method of claim 2, wherein the applying step is performed daily.

7. The method of claim 2, wherein the peptidic hydrolyzate is solubilized in one or more physiologically acceptable solvents, such as water, glycerol, ethanol, propylene glycol, butylene glycol, dipropylene glycol, ethoxylated diethylene glycol or propoxylated diethylene glycol, cyclic polyols, or any mixture of these solvents.

8. The method of claim 2, wherein the solubilized peptidic hydrolyzate comprises at least between 1.5 and 4 g/l of peptidic nature compounds.

9. The method of claim 2, wherein the solubilized hydrolyzate is used in a quantity representing from 0.001% to 5% of the total weight of the composition.

10. The method of claim 2, further comprising a soy peptidic hydrolyzate.

11. The method of claim 10, wherein the non-fermented rice peptidic hydrolyzate and the soy peptidic hydrolyzate are present at concentrations of between 10 and 90%.

12. The method of claim 2, wherein at least 85% of the peptidic nature compounds present in the hydrolyzate are peptides with a size of less than 6 kDa.

13. The method of claim 1, wherein the peptidic hydrolyzate is solubilized in one or more physiologically acceptable solvents, such as water, glycerol, ethanol, propylene glycol, butylene glycol, dipropylene glycol, ethoxylated diethylene glycol or propoxylated diethylene glycol, cyclic polyols, or any mixture of these solvents.

* * * * *